(12) United States Patent
Jang et al.

(10) Patent No.: US 8,738,183 B2
(45) Date of Patent: May 27, 2014

(54) PERSONALLY CUSTOMIZED ELECTRONIC FURNITURE AND METHOD OF IMPLEMENTING THE SAME

(75) Inventors: Woo-young Jang, Seongnam-si (KR); Hyung-kyu Lim, Seoul (KR); Dong-wook Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 614 days.

(21) Appl. No.: 12/349,750

(22) Filed: Jan. 7, 2009

(65) Prior Publication Data

US 2009/0193578 A1  Aug. 6, 2009

(30) Foreign Application Priority Data

Feb. 1, 2008  (KR) .................. 10-2008-0010820
Apr. 30, 2008  (KR) .................. 10-2008-0040824

(51) Int. Cl.
    *G05B 13/00* (2006.01)
(52) U.S. Cl.
    USPC ................................ 700/275; 600/27; 368/10
(58) Field of Classification Search
    USPC .................. 600/26, 27; 368/10; 700/275
    See application file for complete search history.

(56) References Cited

U.S. PATENT DOCUMENTS

| | | | |
|---|---|---|---|
| 5,417,222 A | 5/1995 | Dempsey et al. | |
| 5,813,993 A * | 9/1998 | Kaplan et al. | 600/544 |
| 7,041,049 B1 * | 5/2006 | Raniere | 600/26 |
| 7,304,580 B2 * | 12/2007 | Sullivan et al. | 340/573.1 |
| 7,524,279 B2 * | 4/2009 | Auphan | 600/26 |
| 2004/0111045 A1 * | 6/2004 | Sullivan et al. | 600/595 |
| 2004/0244807 A1 * | 12/2004 | Sun et al. | 128/904 |
| 2005/0143617 A1 * | 6/2005 | Auphan | 600/26 |
| 2006/0106275 A1 * | 5/2006 | Raniere | 600/26 |
| 2006/0183980 A1 * | 8/2006 | Yang | 600/301 |
| 2007/0083079 A1 * | 4/2007 | Lee et al. | 600/27 |

FOREIGN PATENT DOCUMENTS

| | | |
|---|---|---|
| EP | 1 738 961 A1 | 1/2007 |
| JP | 3215472 B2 | 7/2001 |
| KR | 200366830 Y1 | 11/2004 |
| KR | 1020070067288 A | 6/2007 |
| KR | 1020080003399 A | 1/2008 |

OTHER PUBLICATIONS

International Search Report for PCT/KR2009/000449 dated Aug. 18, 2009 and English Translation.
Written Opinion for PCT/KR2009/000449 dated Aug. 18, 2009 and English Translation.

* cited by examiner

*Primary Examiner* — Mohammad Ali
*Assistant Examiner* — Anthony Whittington
(74) *Attorney, Agent, or Firm* — Cantor Colburn LLP

(57) ABSTRACT

An apparatus which provides various functions for physical and/or mental relaxation, as well as for health care of a user, and a method of implementing the apparatus, include downloading personal data of the user from a user terminal to a personally customized bed and controlling one or more functions of the personally customized bed based on the personal data.

32 Claims, 5 Drawing Sheets

PERSONALLY CUSTOMIZED ELECTRONIC FURNITURE AND METHOD OF IMPLEMENTING THE SAME

CROSS-REFERENCE TO RELATED APPLICATIONS

This application claims priority to Korean Patent Application Nos. 10-2008-0010820, filed on Feb. 1, 2008 and 10-2008-0040824, filed on Apr. 30, 2008, and all the benefits accruing therefrom under 35 U.S.C. §119, the contents of which in their entireties are herein incorporated by reference.

BACKGROUND

1. Field

Disclosed herein is an apparatus for providing various functions related to physical and/or mental relaxation of a user, as well as for health care of the user, and a method of implementing the same.

2. Description of the Related Art

As a result of ongoing and rapid industrial development, the air people breathe contains increasing amounts of materials which are harmful to the human body. In addition, disease rates have been continuously increasing due to physical and mental stress, among other things. Furthermore, electromagnetic waves generated by electronic devices, for example, further threaten people's health and well being. Accordingly, development of electronic appliances, such as washing machines which release anions, for example, has been increasingly focused on consideration of public health, instead of merely on improving performance of the electronic appliances.

SUMMARY

Exemplary embodiments of the present invention provide an apparatus for providing various personally customized and optimized functions for physical and mental relaxation and for the health care of a user in consideration of a physical status of the user, and a method of implementing the apparatus.

According to an exemplary embodiment of the present invention, a method of implementing a personally customized bed includes downloading personal data of a user from a user terminal to the personally customized bed and controlling one or more functions of the personally customized bed based on the personal data.

According to an alternative exemplary embodiment of the present invention, there is provided a computer program product comprising a computer readable program code for executing a method of implementing a personally customized bed, and instructions for causing the computer to execute the method. The method includes downloading personal data of a user from a user terminal to the personally customized bed and controlling one or more functions of the personally customized bed based on the personal data.

According to another alternative exemplary embodiment of the present invention, there is provided a personally customized bed including a terminal interface which downloads personal data of a user from a user terminal and a control unit which controls one or more functions of the personally customized bed based on the personal data.

According to another alternative exemplary embodiment of the present invention, there is provided a method of implementing personally customized electronic furniture. The method includes downloading personal data of a user from a user terminal and controlling one or more functions of the personally customized electronic furniture based on the personal data.

According to another alternative exemplary embodiment of the present invention, there is provided a computer program product comprising a computer readable program code for executing a method of implementing personally customized electronic furniture, and instructions for causing the computer to execute the method. The method includes downloading personal data of a user from a user terminal and controlling one or more functions of the personally customized electronic furniture based on the personal data.

According to another of the present invention, there is provided personally customized electronic furniture including a terminal interface which downloads personal data of a user from a user terminal and a control unit which controls one or more functions of the personally customized electronic furniture based on the personal data.

According to another alternative exemplary embodiment of the present invention, there is provided a method of managing sleep of a user on a personally customized bed. The method includes downloading personal data of a user from a user terminal, monitoring a sleeping state of the user based on the personal data, and controlling one or more functions of the personally customized bed based on a result of the monitoring the sleeping state of the user.

According to another alternative exemplary embodiment of the present invention, there is provided a computer program product comprising a computer readable program code for executing a method of managing sleep of a user on a personally customized bed, and instructions for causing a computer to implement the method. The method includes downloading personal data of a user from a user terminal, monitoring a sleeping state of the user based on the personal data, and controlling one or more functions of the personally customized bed based on a result of the monitoring the sleeping state of the user.

According to another alternative exemplary embodiment of the present invention, there is provided an apparatus for managing sleep of a user on a personally customized bed, the apparatus including a terminal interface which downloads personal data of the user from a user terminal, a sensor unit which monitors a sleeping state of the user based on the personal data, and a control unit which controls one or more functions of the personally customized bed based on a result of the monitoring.

BRIEF DESCRIPTION OF THE DRAWINGS

The above and other aspects, features and advantages of the present invention will become more readily apparent by describing in further detail exemplary embodiments thereof with reference to the accompanying drawings, in which.

DETAILED DESCRIPTION

Figure 1:
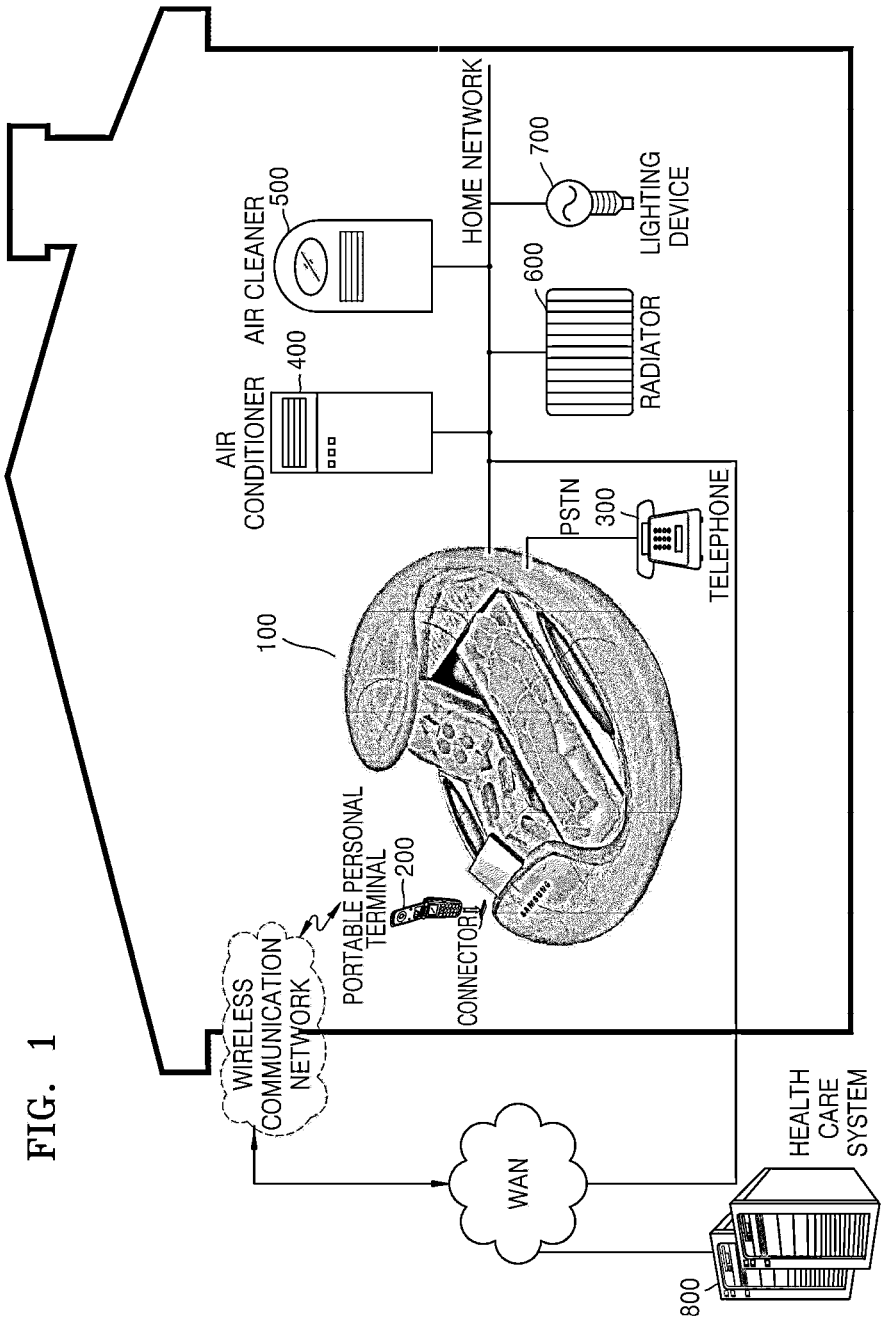
FIG. 1 is a diagram illustrating an exemplary embodiment of a personally customized bed and an installation layout of the personally customized bed, according to the present invention.

The invention will now be described more fully hereinafter with reference to the accompanying drawings, in which exemplary embodiments of the invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the device in one of the figures were turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning which is consistent with their meaning in the context of the relevant art and the present disclosure, and will not be interpreted in an idealized or overly formal sense unless expressly so defined herein.

Exemplary embodiments of the present invention are described herein with reference to cross section illustrations which are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes which result, for example, from manufacturing. For example, a region illustrated or described as flat may, typically, have rough and/or nonlinear features. Moreover, sharp angles which are illustrated may be rounded. Thus, the regions illustrated in the figures are schematic in nature and their shapes are not intended to illustrate the precise shape of a region and are not intended to limit the scope of the present invention.

Hereinafter, exemplary embodiments of the present invention will be described in further detail with reference to the accompanying drawings.

Electronic appliances, such as televisions ("TVs"), refrigerators, and washing machines, for example, are home electronic devices for providing convenience or enjoyment to users of the electronic appliances. In contrast, furniture, such as beds, chairs, and sofas for example, is used primarily to support the human body. In exemplary embodiments of the present invention described herein, the term "electronic furniture" means furniture for providing various electronic functions, e.g., complex integrated objects in which electronic appliances are combined with furniture. For purposes of description herein only, an electronic bed will now be described as an example of a piece of electronic furniture according to an exemplary embodiment of the present invention. However, it will be understood that alternative exemplary embodiments of the present invention are not limited thereto, and may instead be applied to any other type of furniture, such as a chair or a sofa, for example.

FIG. 1 is a diagram illustrating an exemplary embodiment of a personally customized bed 100 and an installation layout of the personally customized bed 100 according to the present invention.

Referring to FIG. 1, the personally customized bed 100 includes a connector, to which a portable personal terminal 200 is mounted, and which is thereafter connected to a home network. In an exemplary embodiment, the personally customized bed 100 is connected to a health care system 800 located at a node on an external wide area network ("WAN"), by using a wireless communication network via a wireless communication function of the portable personal terminal 200 or, alternatively, by using a wired communication function of the home network, for example. In addition, the personally customized bed 100 may be further connected to an air conditioner 400, an air cleaner 500, a radiator 600 and/or a lighting device 700, for example, through the home network. Furthermore, the personally customized bed 100 according to an exemplary embodiment may be connected to a public switched telephone network ("PSTN") through a telephone 300 connected to the personally customized bed 100, as shown in FIG. 1.

Figure 2:
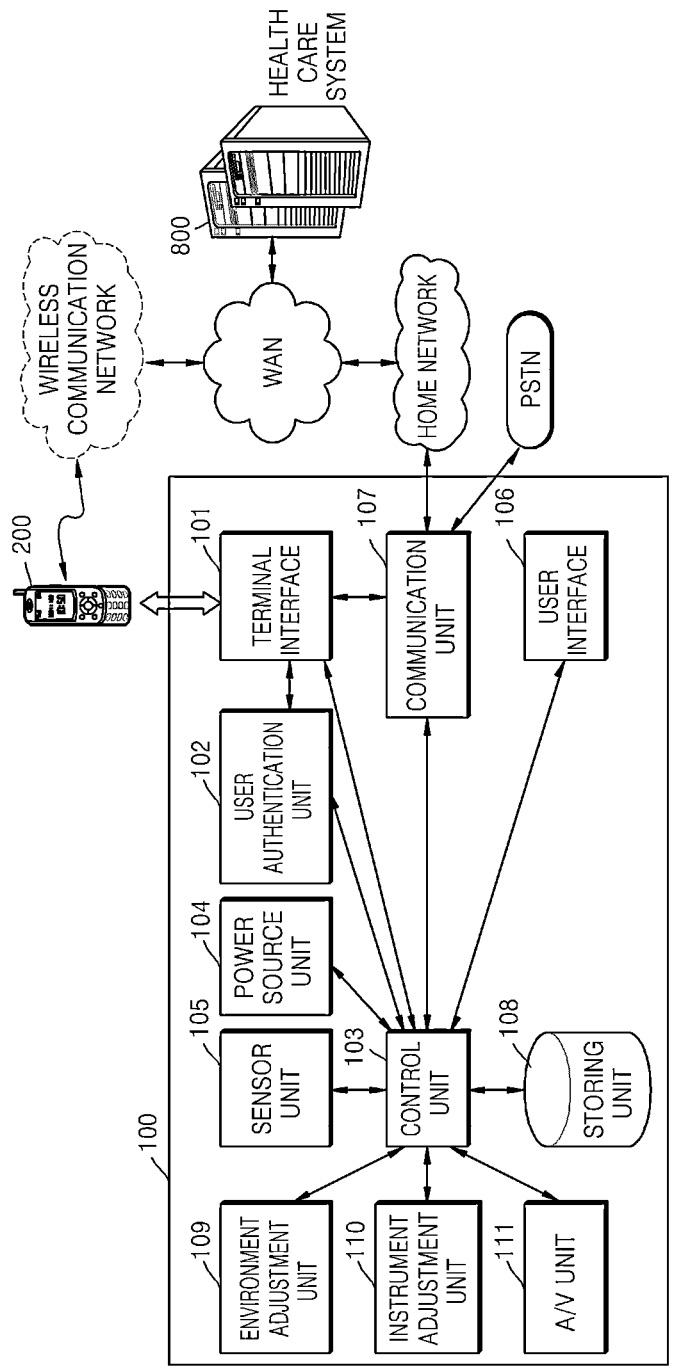
FIG. 2 is a block diagram of an exemplary embodiment of the personally customized bed shown in FIG. 1.

FIG. 2 is a block diagram of an exemplary embodiment of the personally customized bed 100 shown in FIG. 1.

Referring to FIGS. 1 and 2, the personally customized bed 100 includes a terminal interface 101, a user authentication unit 102, a control unit 103, a power source unit 104, a sensor unit 105, a user interface 106, a communication unit 107, a storing unit 108, an environment adjustment unit 109, an instrument adjustment unit 110, and an audio/video ("A/V") unit 111. The personally customized bed 100 is described herein as one example of personally customized electronic furniture and, as noted above, personally customized electronic furniture according to alternative exemplary embodiments of the present invention may include any and all other types of furniture, such as a personally customized chair and a personally customized sofa, for example.

Referring to FIG. 2, the terminal interface 101 detects whether the portable personal terminal 200 is connected to the personally customized bed 100. Specifically, a connector, into which the portable personal terminal 200 is inserted, is mounted on the terminal interface 101. Thus, by inserting the portable personal terminal 200 into the connector, the portable personal terminal 200 is connected to the personally customized bed 100. In an exemplary embodiment, the portable personal terminal 200 is a cellular phone having a communication function, but alternative exemplary embodiments are not limited thereto. For example, the portable personal terminal 200 may be a personal digital assistant ("PDA"), an MPEG ("motion pictures expert group") audio layer 3 ("MP3") player, a notebook computer, or a palm top computer, but alternative exemplary embodiments are not limited to the foregoing list.

Also, the portable personal terminal 200 according to an exemplary current embodiment of the present invention may include a function of measuring biological signals from a user's body. For example, in an exemplary embodiment of the present invention, the portable personal terminal 200 may be a portable medical device having a communication function. More particularly, the portable medical device may be a medical device worn on a user's wrist, similar to a wristwatch, for example, and which measures biological signals such as blood sugar level, blood pressure, and electrocardiogram ("ECG"). In an exemplary embodiment of the present invention, a communication function is included with the portable medical device. It will be understood that any other type of terminal similar to the portable medical device may be used in alternative exemplary embodiments.

Still referring to FIG. 2, the user authentication unit 102 according to an exemplary embodiment determines whether a user of the portable personal terminal 200 is authorized to use the personally customized bed 100, such as by checking a personal identification code of the portable personal terminal 200 connected to the personally customized bed 100, for example. The personally customized bed 100 according to an exemplary embodiment of the present invention may be located in a private house or, alternatively, in a public place such as a hospital, for example. Thus, when the personally customized bed 100 is located in a public place, the user authentication unit 102 prevents indiscriminate use of the personally customized bed 100, such that only a user who is authorized to use the personally customized bed 100 by, for example, paying a fee for the personally customized bed 100, can use the personally customized bed 100. However, when the personally customized bed 100 is located in a private house, the user authentication unit 102 may not be included and/or may not be used in the personally customized bed 100.

When the terminal interface 101 detects that the portable personal terminal 200 is not connected to the personally customized bed 100, or when the user authentication unit 102 determines that the user of the portable personal terminal 200 is not authorized to use the personally customized bed 100, the control unit 103 controls a power supply function of the power source unit 104 to be maintained in a stand-by mode for providing power only to the terminal interface 101, the user authentication unit 102, and the control unit 103. In contrast, when the terminal interface 101 detects that the portable personal terminal 200 is connected to the personally customized bed 100, the control unit 103 controls the power supply function of the power source unit 104 to change from the stand-by mode to an active mode for providing power not only to the terminal interface 101, the user authentication unit 102, and the control unit 103 but also to other elements of the personally customized bed 100. Alternatively, the control unit 103 may control the power supply function of the power source unit 104 from the stand-by mode to the active mode based on whether the user is seated on or is lying on the personally customized bed 100, based on, for example, a detected pressed state of air cells in a mattress of the personally customized bed 100, instead of detecting whether the portable personal terminal 200 is connected to the personally customized bed 100. In an alternative exemplary embodiment, user authentication may be performed by using voice recognition technology.

When the personally customized bed 100 is located in a public place, the control unit 103 controls the power supply function of the power source unit 104 to be changed from the stand-by mode to the active mode when the user authentication unit 102 determines that the user of the portable personal terminal 200 is authorized to use the personally customized bed 100. Also, in the active mode, if the terminal interface 101 detects that the portable personal terminal 200 is not connected to the personally customized bed 100, the control unit 103 controls the power supply function of the power source unit 104 to change from the active mode to the stand-by mode. Put another way, the personally customized bed 100 starts the active mode for operating all functions if the user inserts the portable personal terminal 200 into the connector of the terminal interface 101, and the personally customized bed 100 starts the stand-by mode only for detecting whether the portable personal terminal 200 is connected to the personally customized bed 100 if the user separates the portable personal terminal 200 from the connector of the terminal interface 101.

In addition, the control unit 103 controls a communication function of the communication unit 107, such as to download personal data of the user from the portable personal terminal 200, or to connect the personally customized bed 100 to the health care system 800 located in a remote place, such as through a network, or to transmit a certain message to a rescue party (e.g., to call "911") or to a physician by phone through a PSTN, for example. Furthermore, the control unit 103 controls a sensing function of the sensor unit 105 to sense an environment substantially around the personally customized bed 100 and/or to measure biological signals of the user. As such, the control unit 103 controls one or more functions provided by the personally customized bed 100 based on at least one of the personal data downloaded by the communication unit 107, remote control information received by the communication unit 107, environment information obtained by the sensor unit 105, and direct control information received from the user, for example, by the user interface 106. According to an exemplary embodiment of the present invention, the functions provided by the personally customized bed 100 include not only the power supply function of the power source unit 104, the communication function of the communication unit 107, and the sensing function of the sensor unit 105, but also an environment adjustment function of the environment adjustment unit 109, an instrument operation adjustment function of the instrument adjustment unit 110, and an A/V content output adjustment function of the A/V unit 111.

In an exemplary embodiment of the present invention, examples of the personal data of the user include, but are not limited to, physical state information, private information, health care history information, and A/V content preference information of the user. Examples of the physical state information include biological signals measured by a measurement device of the portable personal terminal 200 and biological signals measured by a measurement device of the personally customized bed 100, but exemplary embodiments of the present invention are not limited thereto. Thus, the control unit 103 may control a physical and mental relaxation function, as well as a health care function provided by the personally customized bed 100, based on the physical status information of the user obtained from the personal data downloaded by the communication unit 107. Also, if a biological signal measured by the measurement device of the portable personal terminal 200 or a biological signal measured by the measurement device of the personally customized bed 100 indicates an emergency, such as a heart attack of the user, for example, the control unit 103 controls the communication function of the communication unit 107 to inform, in real time, a rescue party and/or a physician about the emergency.

IN an exemplary embodiment, examples of the biological signals include, but are not limited to, electrocardiograph ("ECG") signals, oxygen saturation ("SpO$_2$"), electroencephalogram ("EEG") signals, blood pressure, pulse rate, breathing rate and body temperature of the user. In some cases, however, due to restrictions of volume and weight of the portable personal terminal 200, some of the biological signals may be easily measured by the portable personal terminal 200 while other biological signals may not. For example, the body temperature of the user may be easily measured when the user holds the portable personal terminal 200 in a hand. Thus, in an exemplary embodiment of the present invention, the sensor unit 105 of the personally customized bed 100 may be designed to measure other biological signals which are not easily measured by the portable personal terminal 200.

Examples of the private information include, but are not limited to, gender, age, height, weight and a daily schedule of the user. Examples of the health care history information may be preference information regarding content from A/V components, preference information about the environment (for example, temperature, humidity, and illumination level) around the personally customized bed 100, and preference information regarding certain massage type by operation of a mechanical frame and the air cells included in the mattress of the personally customized bed 100, for example, but not being limited thereto, all of which are represented by a health care history of the user. In an exemplary embodiment, the health care history information may be generated based on previous health care history information of the user, may be manually set in real time by a health care expert, and/or may be automatically set by the health care system 800.

In particular and with regard to the age of the user in the private information, the control unit 103 according to an exemplary embodiment controls a sensing function of the sensor unit 105 to more frequently measure the ECG based on the age. More specifically, the older the user is, the more frequently the ECG is measured, to more frequently monitor for heart attack in older aged users, for example. In addition and regarding the user height data in the private information, the control unit 103 according to an exemplary embodiment may control the instrument operation adjustment function of the instrument adjustment unit 110 to operate the mechanical frame and the air cells included in the mattress of the personally customized bed 100 based on the height of the user. Thus, a massage function is optimized to the height of the user.

The power source unit 104 changes a power state of the personally customized bed 100 from the stand-by mode to the active mode, or from the active mode to the stand-by mode, based on a control signal, for example, from the control unit 103.

The sensor unit 105 obtains the environment information and the physical state information by sensing the environment around the personally customized bed 100 and a physical state of the user, and is also controlled by the control unit 103. For example, the sensor unit 105 according to an exemplary embodiment obtains the environment information by sensing humidity, temperature, illumination level, noise level, vibration level, dust amount and oxygen amount, for example, around, e.g., proximate to, the personally customized bed 100. Also, the sensor unit 105 obtains the physical state information by sensing the biological signals of the user, as described in greater detail above. In particular, the sensor unit 105 according to an exemplary embodiment measures a biological signal which may not be easily measured by the portable personal terminal 200, based on selection information of the user, which is received through the user interface 106. Also, the sensor unit 105 senses a state of the personally customized bed 100 by the control of the control unit 103. For example, the sensor unit 105 senses the pressed state of the air cells in the mattress of the personally customized bed 100, or a local clock value of the personally customized bed 100, by the control of the control unit 103.

The user interface 106 receives selection information indicating, for example, whether a biological signal of the user has been measured, and selection information indicating whether to connect the personally customized bed 100 to the health care system 800, located at a remote place, from the user of the portable personal terminal 200. Also, the user interface 106 receives the direct control information for directly and manually controlling the personally customized bed 100 by the user. Furthermore, if the user authentication unit 102 determines that the user of the portable personal terminal 200 is not authorized to use the personally customized bed 100, the user interface 106 may receive new personal data or new user authorization information such as fee pay information.

In an exemplary embodiment, the communication unit 107 downloads the personal data of the user from the portable personal terminal 200, by the control of the control unit 103. Also, the communication unit 107 may be connected to a network by using the wireless communication function of the portable personal terminal 200, by the control of the control unit 103, may connect the personally customized bed 100 to the health care system 800 located in a remote place, such as a node on a WAN, through the connected network or a home network, and may perform consultation with an expert about health care, access an online community through the health care system 800, or receive the remote control information on the personally customized bed 100 from the health care system 800.

Figure 3:
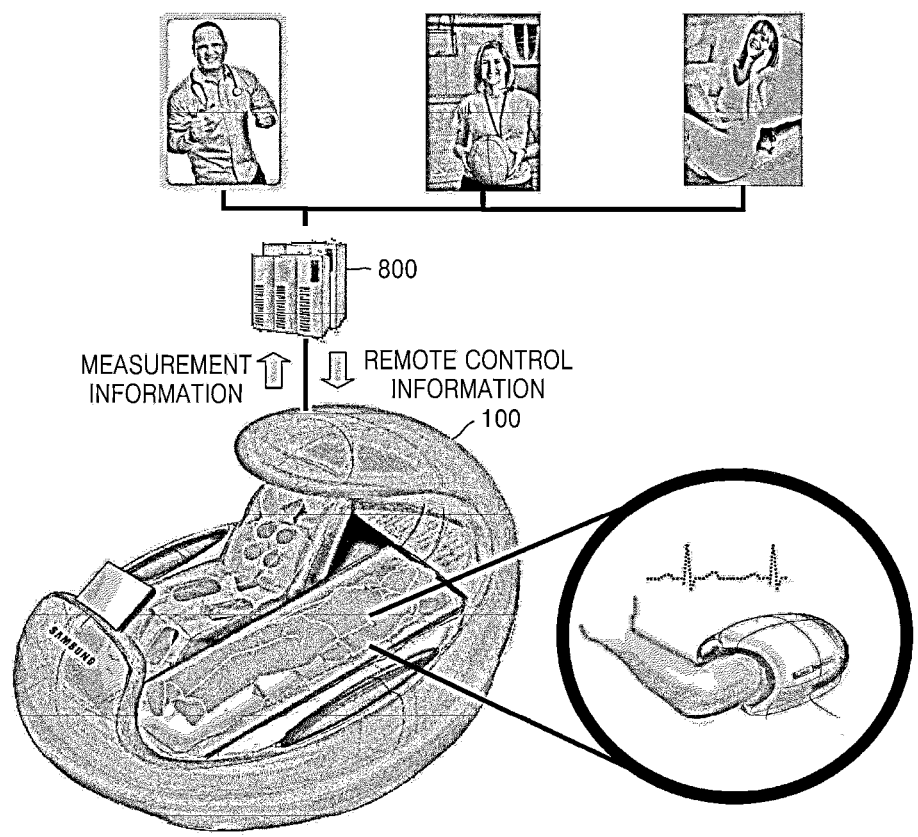
FIG. 3 is a diagram of an exemplary embodiment of remote medical service provided using a communication unit according to the present invention.

FIG. 3 is a diagram of an exemplary embodiment of a remote medical service provided through the communication unit 107 according to the present invention.

Referring to FIGS. 2 and 3, the communication unit 107 transmits information on biological signals of a user, which are measured by the sensor unit 105, to the health care system 800 through a network. Then, the user may consult with a physician or an expert managing the health care system 800 on line. The physician or the expert inputs remote control information on the personally customized bed 100 to the health care system 800 based on a result of the online consultation and measurement information transmitted from the personally customized bed 100, and then the remote control information is transmitted to the personally customized bed 100 through the network. As a result, according to an exemplary embodiment of the present invention, the remote medical service is quickly, conveniently and easily provided.

In an exemplary embodiment, the communication unit 107 may transmit a message stored in the storing unit 108 to a rescue party (to call "911", for example), or a physician, by phone through a PSTN, by the control of the control unit 103. The communication unit 107 may store the downloaded or received information in the storing unit 106 via the control unit 103. Furthermore, the communication unit 107 may function as a library of A/V contents having a large capacity by sequentially and accumulatively storing A/V contents downloaded from the portable personal terminal 200 in the storing unit 108. In an exemplary embodiment of the present invention, the storing unit 106 may be a hard disk, for example, but alternative exemplary embodiments of the present invention are not limited thereto.

Referring again to FIG. 2, the environment adjustment unit 109 adjusts the environment around the personally customized bed 100, based on the control of the control unit 103. For example, the environment adjustment unit 109 adjusts at least one of humidity, temperature, illumination level, noise level, vibration level, dust amount and oxygen amount around the personally customized bed 100. In particular, the environment adjustment unit 109 may include a device having a function for adjusting humidity, temperature, illumination level, noise level, vibration level, dust amount and oxygen amount around the personally customized bed 100.

The instrument adjustment unit 110 adjusts instrument operation of the personally customized bed 100, based on the control of the control unit 103. More specifically, the instrument adjustment unit 110 adjusts operation of at least one of the mechanical frame and the air cells included in the mattress of the personally customized bed 100. Thus, the mattress of the personally customized bed 100 includes a mechanical variable frame and a plurality of air cells to physically massage or stretch the user. More particularly, each of the air cells includes a driving instrument for stimulating the body of the user. By using driving instruments, various parts of the body of the user may be separately stimulated. In addition, the instrument adjustment unit 110 may adjust a releasing amount of an aroma releasing instrument included in the personally customized bed 100, by the control of the control unit 103. Also, the instrument adjustment unit 110 may move an instrument such as a display panel or a speaker, from an external position to an internal position of the personally customized bed 100, by the control of the control unit 103.

The A/V unit 111 selects A/V content and adjusts an output state of the selected A/V content, by the control of the control unit 103. More specifically, the A/V unit 111 adjusts at least one of an image output of the display panel of the personally customized bed 100 and a speech output of the speaker of the personally customized bed 100, by the control of the control unit 103. For example, the A/V unit 111 may output the daily schedule of the user through the display panel or output psychotherapy music or a fire alarm through the speaker, by the control of the control unit 103.

Figure 4:
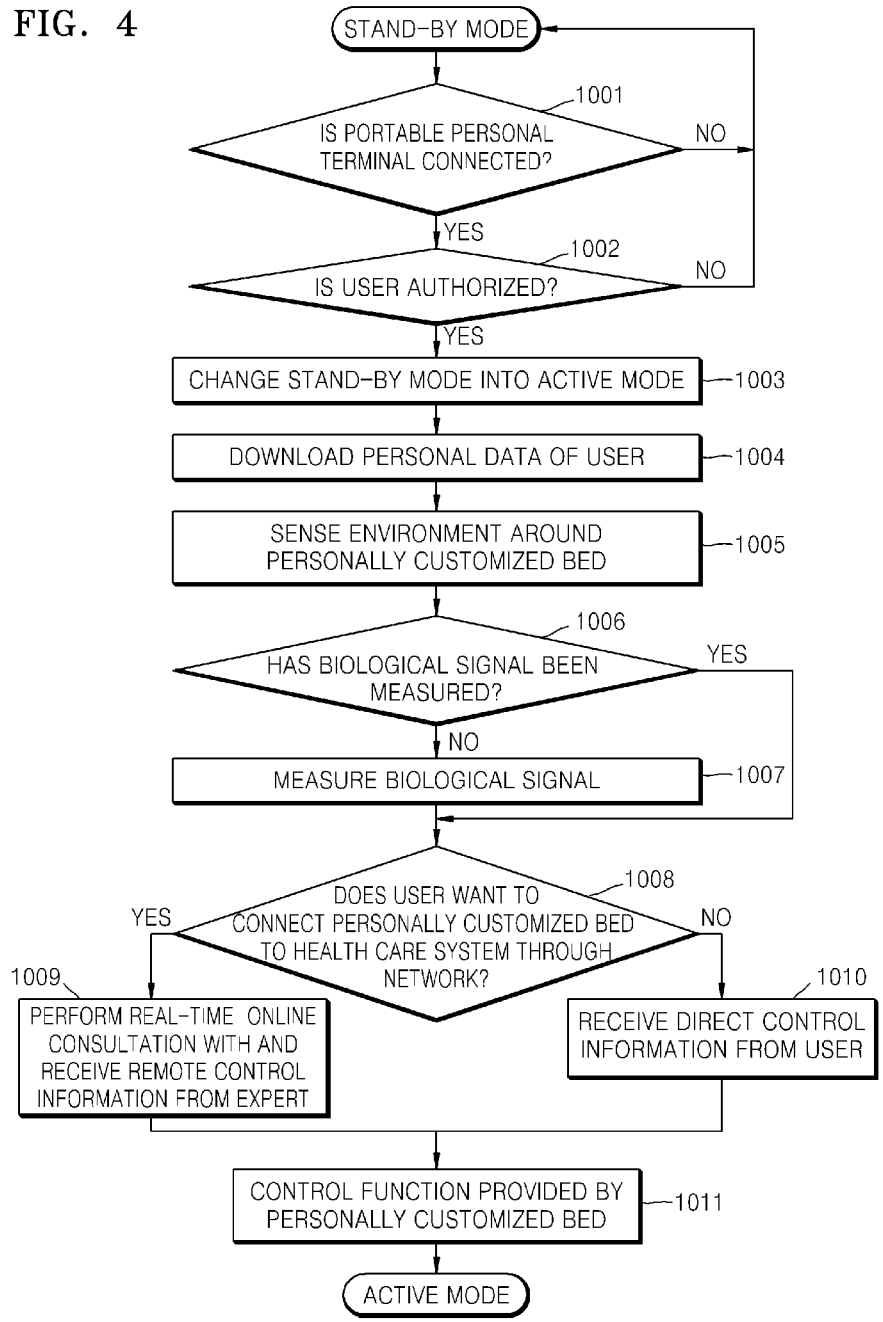
FIG. 4 is a flowchart of an exemplary embodiment of a method of implementing a personally customized bed according to the present invention.

FIG. 4 is a flowchart of an exemplary embodiment of a method of implementing a personally customized bed according to the present invention.

A method according to an exemplary embodiment of the present invention corresponds to a serial time process, for example, of the personally customized bed 100 according to the exemplary embodiment shown in FIG. 2 and described in greater detail above with reference thereto. Thus, the method described herein is in conjunction with the personally customized bed 100 shown in FIG. 2, and any repetitive detailed description thereof will hereinafter be omitted.

Referring now to FIG. 4, in operation 1001, the terminal interface 101 detects whether the portable personal terminal 200 is connected to the personally customized bed 100. If the portable personal terminal 200 is connected to the personally customized bed 100, the method proceeds to operation 1002. Otherwise, a power state of the personally customized bed 100 is maintained in a stand-by mode.

In operation 1002, the user authentication unit 102 determines whether a user of the portable personal terminal 200 is authorized to use the personally customized bed 100, by checking a personal identification code of the portable personal terminal 200, for example. If the user authentication unit 102 determines that the user of the portable personal terminal 200 is authorized to use the personally customized bed 100, the method proceeds to operation 1003. Otherwise, the power state of the personally customized bed 100 is maintained in the stand-by mode.

In operation 1003, the control unit 103 controls a power supply function of the power source unit 104 such that the power state of the personally customized bed 100 is changed from the stand-by mode to an active mode. By the control of the control unit 103, the power source unit 104 changes the power state of the personally customized bed 100 from the stand-by mode to the active mode.

In operation 1004, the control unit 103 controls a communication function of the communication unit 107 to download personal data of the user from the portable personal terminal 200. Based on control of the control unit 103, the communication unit 107 downloads the personal data of the user from the portable personal terminal 200.

In operation 1005, the control unit 103 controls a sensing function of the personally customized bed 100 to sense the environment around the personally customized bed 100. Based on the control of the control unit 103, the sensor unit 105 obtains environment information by sensing the environment around the personally customized bed 100.

In operation 1006, the user interface 106 receives selection information indicating whether a biological signal of the user has been measured, from the user of the portable personal terminal 200. If the selection information indicates that the biological signal of the user has not been measured, the method proceeds to operation 1007. Otherwise, the method proceeds to operation 1008.

In operation 1007, the control unit 103 controls the sensing function of the personally customized bed 100 to measure the biological signal of the user. By the control of the control unit 103, the sensor unit 105 obtains physical state information by sensing the biological signal of the user.

In operation 1008, the user interface 106 receives selection information indicating whether to connect the personally customized bed 100 to the health care system 800 located in a remote place, for example. If the selection information indicates to connect the personally customized bed 100 to the health care system 800, the method proceeds to operation 1009. Otherwise, the method proceeds to operation 1010.

In operation 1009, the control unit 103 controls the communication function of the personally customized bed 100 to connect the personally customized bed 100 to the health care system 800 through a network. By the control of the control unit 103, the communication unit 107 connects the personally customized bed 100 to the health care system 800 through the network, and performs consultation with an expert about health care and/or accesses an online community through the health care system 800, or receives remote control information of the expert on the personally customized bed 100 from the health care system 800.

In operation 1010, the user interface 106 receives direct control information that is input by the user.

In operation 1011, the control unit 103 controls one or more functions provided by the personally customized bed 100, based on at least one of the personal data downloaded in operation 1004, the environment information obtained in operation 1005, the remote control information received in operation 1009, and the direct control information received in operation 1010.

According to an exemplary embodiment of the present invention, a personally optimized electronic bed is implemented by controlling functions for physical and/or mental relaxation and for the health care of a user, which are provided by the personally optimized electronic bed, based on personal data received from a user terminal, such as, for example, information on a physical state of the user, which is measured by the user terminal. In addition, environmental factors, such as humidity, temperature, and illumination level, a massage function, and A/V content for psychotherapy, for example, may be personally optimized and provided to the user. As stated above, alternative exemplary embodiments of the present invention include other types of electronic furniture providing substantially the same or like functions as described herein.

Still referring to FIG. 4, in the operation 1011, various scenarios are possible for physical and/or mental relaxation and for the health care of a user. In an exemplary embodiment, these scenarios may be stored in the storing unit 108 in the form of a computer program. A scenario stored in the storing unit 108 may be implemented by controlling each element of the personally customized bed 100 based on the scenario. More specifically, the personally customized bed 100 according to an exemplary embodiment is configured such that the user may select one of the scenarios stored in the storing unit 108. For example, a scenario for managing sleep of a user will now be described in further detail. It will be noted that various other scenarios for physical and/or mental relaxation and/or for the health care of a user, in addition to the scenario described below, are included in alternative exemplary embodiments of the present invention.

Figure 5:
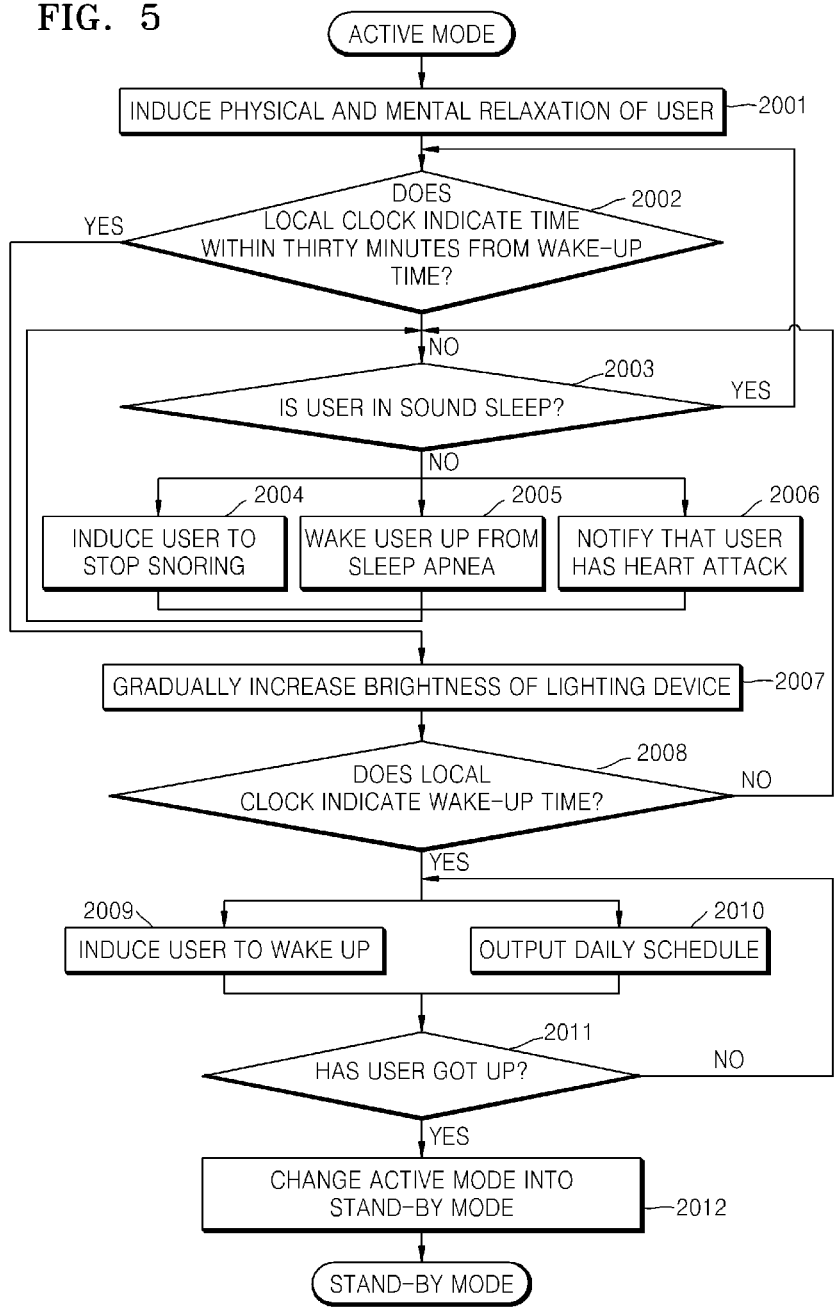
FIG. 5 is a flowchart of an exemplary embodiment of a method of managing sleep of a user according to the present invention.

FIG. 5 is a flowchart of an exemplary embodiment of a method of managing sleep of a user on the personally customized bed 100 according to the present invention.

Referring to FIGS. 2 and 5, in operation 2001, the control unit 103 controls one or more functions provided by the personally customized bed 100 to provide, e.g., to facilitate, physical and/or mental relaxation such that the user experiences sound sleep. For example, the control unit 103 may control the environment around the personally customized bed 100 such that a brightness of a lighting device, e.g., a lamp or other light source, attached to the personally customized bed 100 or, alternatively, a lighting device in a room where the personally customized bed 100 is located, is gradually reduced or increased, depending on the time of day, for example. In an exemplary embodiment, a degree of the brightness of the lighting device and/or a variation speed of the brightness of the lighting device are determined by at least one of the personal data downloaded in operation 1004, the environment information obtained in operation 1005, the remote control information received in operation 1009, and the direct control information received in operation 1010, as described in greater detail above with reference to FIG. 4.

In operation 2002, the sensor unit 105 determines whether a local clock of the personally customized bed 100 indicates a time within a predetermined range of time, such as thirty minutes from wake-up time of the user, for example, by the control of the control unit 103. If the sensor unit 105 determines that the local clock of the personally customized bed 100 indicates a time within the predetermined range of time from the wake-up time of the user, the method proceeds to operation 2007. Otherwise, the method proceeds to operation 2003. In an exemplary embodiment, the certain range of time and the wake-up time of the user are determined by at least one of the personal data downloaded in operation 1004, the environment information obtained in operation 1005, the remote control information received in operation 1009, and the direct control information received in operation 1010, which are described in greater detail above with reference to FIG. 4.

In operation 2003, the sensor unit 105 monitors a sleeping state of the user by measuring biological signals of the user, such as pulse rate and breathing rate, for example, by the control of the control unit 103. If it is determined that the user is in a sound sleep, e.g., the user is sleeping soundly, the method returns to operation 2002. Otherwise, the method proceeds to at least one of operations 2004 through 2006. More specifically, the method proceeds to operation 2004 if the sensor unit 105 senses a snoring sound from the user which is above a threshold decibel level, for example. Likewise, the method proceeds to operation 2005 if the sensor unit 105 senses sleep apnea affecting the user, above a threshold period of time, while the method proceeds to operation 2006 if the sensor unit 105 senses a heart attack of the user. In an exemplary embodiment, the threshold decibel level, the threshold period of time, and a reference value of a heart attack are determined based on at least one of the personal data downloaded in operation 1004, the environment information obtained in operation 1005, the remote control information received in operation 1009, and the direct control information received in operation 1010, for example, each of which are described in greater detail above with reference to FIG. 4.

In operation 2004, the instrument adjustment unit 110 vibrates a mattress of the personally customized bed 100 by the control of the control unit 103, or the A/V unit 111 outputs noise through a speaker of the personally customized bed 100 by the control of the control unit 103. Thus, the user may be notified so that he or she may stop snoring. Further, an operation type of a mechanical frame and air cells included in the mattress and an output degree of an A/V content are determined by at least one of the personal data downloaded in operation 1004, the environment information obtained in operation 1005, the remote control information received in operation 1009, and the direct control information received in operation 1010, which are described in greater detail above with reference to FIG. 4.

In operation 2005, the instrument adjustment unit 110 violently vibrates the mattress of the personally customized bed 100, or the A/V unit 111 outputs a large noise through the speaker of the personally customized bed 100, by the control of the control unit 103. As such, the user wakes up, and thus, the sleep apnea is stopped. To this end, the operation type of the mechanical frame and the air cells included in the mattress and the output degree of the A/V content are determined by using at least one of the personal data downloaded in operation 1004, the environment information obtained in operation 1005, the remote control information received in operation 1009, and the direct control information received in operation 1010, which are described in greater detail above with reference to FIG. 4.

In operation 2006, the communication unit 107 transmits a message, indicating that the user has had a heart attack, to a rescue party (by calling "911", for example) or to a physician by phone in real time, by the control of the control unit 103. In an exemplary embodiment, a phone number of the rescue party or the physician, and/or an emergency call number are determined based on at least one of the personal data downloaded in operation 1004, the environment information obtained in operation 1005, the remote control information received in operation 1009, and the direct control information received in operation 1010, which are described in greater detail above with reference to FIG. 4.

In operation 2007, the environment adjustment unit 109 gradually increases brightness of a lighting device attached to the personally customized bed 100 or a lighting device of a room where the personally customized bed 100 is located, by the control of the control unit 103. In an exemplary embodiment, a degree of the brightness of the lighting device and/or a variation speed of the brightness of the lighting device are determined based on at least one of the personal data downloaded in operation 1004, the environment information obtained in operation 1005, the remote control information received in operation 1009, and the direct control information received in operation 1010, which are described in greater detail above with reference to FIG. 4.

In operation 2008, the sensor unit 105 determines whether the local clock of the personally customized bed 100 indicates the wake-up time of the user, by the control of the control unit 103. If the sensor unit 105 determines that the local clock of the personally customized bed 100 indicates the wake-up time of the user, the method proceeds to operation 2009. Otherwise, the method returns to operation 2003.

In operation 2009, the control unit 103 controls the one or more functions provided by the personally customized bed 100 in order to provide physical and/or mental stimulation, thus inducing the user to wake up. For example, the control unit 103 according to an exemplary embodiment controls an instrument operation adjustment function of the personally customized bed 100 in such a manner that the body of the user is stretched by operation of the mechanical frame included in the mattress of the personally customized bed 100. Thus, an operation type of a health care instrument is determined by using at least one of the personal data downloaded in operation 1004, the environment information obtained in operation 1005, the remote control information received in operation 1009, and the direct control information received in operation 1010, which are described in greater detail above with reference to FIG. 4.

In operation 2010, the A/V unit 111 outputs a daily schedule of the user through a display panel attached to the personally customized bed 100, by the control of the control unit 103. In an exemplary embodiment, an output type of an A/V content is determined by using at least one of the personal data downloaded in operation 1004, the environment information obtained in operation 1005, the remote control information received in operation 1009, and the direct control information received in operation 1010, which are described in greater detail above with reference to FIG. 4.

In operation 2011, the sensor unit 105 determines whether the user has got up, e.g., has sat up or has gotten out of the personally customized bed 100, by measuring a pressed state of the air cells in the mattress of the personally customized bed 100. If the sensor unit 105 determines that the user has got up, the method proceeds to operation 2012. Otherwise, the method returns to operations 2009 and 2010.

In operation 2012, the power source unit 104 changes a power state of the personally customized bed 100 from an active mode to a stand-by mode, by the control of the control unit 103.

According to exemplary embodiments of the present invention as described herein, an apparatus provides various personally customized and/or optimized functions for physical and mental relaxation, as well as for health care of a user, based on a physical status of the user.

The present invention should not be construed as being limited to the exemplary embodiments set forth herein. Rather, these exemplary embodiments are provided so that this disclosure will be thorough and complete and will fully convey the concept of the present invention to those skilled in the art. For example, it will be noted that exemplary embodiments of the present invention can be written as computer programs and can be implemented in computers such as general-use digital computers, for example, which execute the programs using a computer readable recording medium. In addition, the data used in the exemplary embodiments of the present invention described herein may be recorded on a computer readable recording medium in various ways and forms. Examples of the computer readable recording medium include, but are not limited to, magnetic storage media, such as read only memory ("ROM"), floppy disks, and/or hard disks, for example, as well as optical recording media such as CD-ROMs and/or DVDs, although alternative exemplary embodiments of the present invention are not limited to the foregoing lists.

While the present invention has been particularly shown and described with reference to exemplary embodiments thereof, it will be understood by those of ordinary skill in the art that various changes in form and details may be made therein without departing from the spirit or scope of the present invention as defined by the following claims.

What is claimed is:

1. A method of implementing a personally customized bed, the method comprising:
   detecting whether a portable user terminal is connected to the personally customized bed;
   downloading, when the portable user terminal is connected to the personally customized bed, personal data of a user from the portable user terminal to the personally customized bed connected to the portable user terminal, the personal data including at least one of physical state information of the user, private information of the user, health care history information of the user and audio/video content preference information of the user;
   controlling one or more functions of the personally customized bed based on the personal data downloaded from the portable user terminal; and
   connecting the personally customized bed to a health care system through a network when the connection to the health care system is selected through user interface, and performing consultation with an expert about health care,
   wherein the personal data is not directly measured from the user but downloaded from the portable user terminal, and includes non-sleep related private personal information.

2. The method of claim 1, wherein the controlling the one or more functions of the personally customized bed is based on a physical state of the user represented by the personal data.

3. The method of claim 2, wherein the physical state of the user comprises at least one of a biological signal of the user measured by a measurement device of the portable user terminal, and a biological signal of the user measured by a measurement device of the personally customized bed.

4. The method of claim 1, further comprising receiving remote control information, through a network, from a health care system located in a remote place,
   wherein the controlling the one or more functions of the personally customized bed is based on the remote control information.

5. The method of claim 4, wherein the receiving the remote control information comprises connecting to the network by using a wireless communication function of the portable user terminal and receiving the remote control information through the network.

6. The method of claim 1, further comprising determining whether the user is authorized to use the personally customized bed by checking a personal identification code of the personal data of the user,
   wherein the controlling the one or more functions of the personally customized bed is based on a result of the determining whether the user is authorized to use the personally customized bed.

7. The method of claim 1, wherein the one or more functions comprise an environment adjustment function, an instrument operation adjustment function and an audio/visual content output adjustment function of the personally customized bed.

8. The method of claim 7, further comprising adjusting at least one of humidity, temperature, illumination level, noise level, vibration level, dust amount and oxygen amount proximate to the personally customized bed, by controlling the environment adjustment function.

9. The method of claim 8, wherein the personally customized bed comprises at least one device which separately adjusts humidity, temperature, illumination level, noise level, vibration level, dust amount and oxygen amount proximate to the personally customized bed.

10. The method of claim 7, further comprising adjusting an operation of at least one of a mechanical frame and a plurality of air cells included in a mattress of the personally customized bed by controlling the instrument operation adjustment function.

11. The method of claim 7, further comprising adjusting at least one of an image output of a display panel of the personally customized bed and a speech output of a speaker of the personally customized bed by controlling the audio/visual content output adjustment function.

12. The method of claim 1, wherein the portable user terminal comprises one of a cellular phone, a personal digital assistant, an audio player, a notebook computer and a palm top computer.

13. A non-transitory computer program product comprising a computer readable program code for executing a method of implementing a personally customized bed, and instructions for causing a computer to implement the method, the method comprising:
   detecting whether a portable user terminal is connected to the personally customized bed,
   downloading, when the portable user terminal is connected to the personally customized bed, personal data of a user from the portable user terminal to the personally customized bed connected to the portable user terminal, the personal data including at least one of physical state information of the user, private information of the user, health care history information of the user and audio/video content preference information of the user;
   controlling one or more functions of the personally customized bed based on the personal data downloaded from the portable user terminal; and
   connecting the personally customized bed to a health care system through a network when the connection to the health care system is selected through user interface, and performing consultation with an expert about health care,
   wherein the personal data is not directly measured from the user but downloaded from the portable user terminal, and includes non-sleep related private personal information.

14. A personally customized bed comprising:
   a terminal interface which downloads, when a portable user terminal is connected thereto, personal data of a user from the connected portable user terminal, the personal data including at least one of physical state information of the user, private information of the user, health care history information of the user and audio/video content preference information of the user; and
   a control unit which controls one or more functions of the personally customized bed based on the personal data downloaded from the portable user terminal, and connects the personally customized bed to a health care system through a network when the connection to the health care system is selected through user interface,
   wherein the personal data is not directly measured from the user but downloaded from the portable user terminal, and includes non-sleep related private personal information.

15. The personally customized bed of claim 14, wherein
   the terminal interface comprises a connector connected to the portable user terminal, and
   the personal data is downloaded when the portable user terminal is connected to the personally customized bed by the connector.

16. A method of implementing personally customized electronic furniture, the method comprising:
   detecting whether a portable user terminal is connected to the personally customized electronic furniture;
   downloading, when the portable user terminal is connected to the personally customized electronic furniture, personal data of a user from the portable user terminal to the personally customized electronic furniture connected to the portable user terminal, the personal data including at least one of physical state information of the user, private information of the user, health care history information of the user and audio/video content preference information of the user;
   controlling one or more functions of the personally customized electronic furniture based on the personal data downloaded from the portable user terminal; and
   connecting the personally customized electronic furniture to a health care system through a network when the connection to the health care system is selected through user interface, and performing consultation with an expert about health care,
   wherein the personal data is not directly measured from the user but downloaded from the portable user terminal, and includes non-sleep related private personal information.

17. The method of claim 16, wherein the controlling the one or more functions of the personally customized electronic furniture is based on a physical state of the user represented by the personal data.

18. The method of claim 17, wherein the physical state of the user comprises at least one of a biological signal of the user measured by a measurement device of the portable user terminal and a biological signal of the user measured by a measurement device of the personally customized electronic furniture.

19. The method of claim 16, further comprising receiving remote control information, through a network, from a health care system located in a remote place,
wherein the controlling the one or more functions of the personally customized electronic furniture is based on the remote control information.

20. The method of claim 19, wherein the receiving the remote control information comprises connecting to the network by using a wireless communication function of the portable user terminal and receiving the remote control information through the network.

21. The method of claim 16, further comprising determining whether the user is authorized to use the personally customized electronic furniture by checking a personal identification code of the personal data,
wherein the controlling the one or more functions of the personally customized electronic furniture is based on a result of the determining.

22. The method of claim 16, wherein the one or more functions of the personally customized electronic furniture comprise an environment adjustment function, an instrument operation adjustment function and an audio/visual content output adjustment function of the personally customized electronic furniture.

23. The method of claim 22, further comprising adjusting at least one of humidity, temperature, illumination level, noise level, vibration level, dust amount and oxygen amount proximate to the personally customized electronic furniture by controlling the environment adjustment function.

24. The method of claim 22, further comprising adjusting an operation of at least one of a mechanical frame and a plurality of air cells included in a mattress of the personally customized electronic furniture by controlling the instrument operation adjustment function.

25. The method of claim 22, further comprising adjusting at least one of an image output of a display panel of the personally customized electronic furniture and a speech output of a speaker of the personally customized electronic furniture by controlling the audio/visual content output adjustment function.

26. The method of claim 16, wherein the portable user terminal comprises one of a cellular phone, a personal digital assistant, an audio player, a notebook computer and a palm top computer.

27. A non-transitory computer program product comprising a computer readable program code for executing a method of implementing personally customized electronic furniture, and instructions for causing a computer to implement the method, the method comprising:
detecting whether a portable user terminal is connected to the personally customized electronic furniture;
downloading, when the portable user terminal is connected to the personally customized electronic furniture, personal data of a user from the portable user terminal connected to the personally customized electronic furniture, the personal data including at least one of physical state information of the user, private information of the user, health care history information of the user and audio/video content preference information of the user;
controlling one or more functions of the personally customized electronic furniture based on the personal data downloaded from the portable user terminal; and
connecting the personally customized electronic furniture to a health care system through a network when the connection to the health care system is selected through user interface, and performing consultation with an expert about health care,
wherein the personal data is not directly measured from the user but downloaded from the portable user terminal, and includes non-sleep related private personal information.

28. Personally customized electronic furniture comprising:
a terminal interface which downloads, when a portable user terminal is connected thereto, personal data of a user from the connected portable user terminal, the personal data including at least one of physical state information of the user, private information of the user, health care history information of the user and audio/video content preference information of the user;
a control unit which controls one or more functions of the personally customized electronic furniture based on the personal data downloaded from the portable user terminal; and connects the personally customized electronic furniture to a health care system through a network when the connection to the health care system is selected through user interface,
wherein the personal data is not directly measured from the user but downloaded from the portable user terminal, and includes non-sleep related private personal information.

29. The personally customized electronic furniture of claim 28, wherein
the terminal interface comprises a connector connected to the portable user terminal, and
the personal data is downloaded when the portable user terminal is connected to the personally customized electronic furniture by the connector.

30. A method of managing sleep of a user on a personally customized bed, the method comprising:
detecting whether a portable user terminal is connected to the personally customized bed;
downloading, when the portable user terminal is connected to the personally customized bed, personal data of the user from the portable user terminal connected to the personally customized bed, the personal data including at least one of physical state information of the user, private information of the user, health care history information of the user and audio/video content preference information of the user;
monitoring a sleeping state of the user based on the personal data downloaded from the portable user terminal; and
controlling one or more functions of the personally customized bed based on a result of the monitoring; and
connecting the personally customized bed to a health care system through a network when the connection to the health care system is selected through user interface, and performing consultation with an expert about health care,
wherein the personal data is not directly measured from the user but downloaded from the portable user terminal, and includes non-sleep related private personal information.

31. A non-transitory computer program product comprising a computer readable program code for executing a method of managing sleep of a user on a personally customized bed, and instructions for causing a computer to implement the method, the method comprising:

detecting whether a portable user terminal is connected to the personally customized bed;

downloading, when the portable user terminal is connected to the personally customized bed, personal data of the user from the portable user terminal connected to the personally customized bed, the personal data including at least one of physical state information of the user, private information of the user, health care history information of the user and audio/video content preference information of the user;

monitoring a sleeping state of the user based on the personal data downloaded from the portable user terminal; and controlling one or more functions of the personally customized bed based on a result of the monitoring; and connecting the personally customized bed to a health care system through a network when the connection to the health care system is selected through user interface, and performing consultation with an expert about health care, wherein the personal data is not directly measured from the user but downloaded from the portable user terminal, and includes non-sleep related private personal information.

32. An apparatus for managing sleep of a user on a personally customized bed, the apparatus comprising:

a terminal interface which, when a portable user terminal is connected thereto, downloads personal data of the user from the connected portable user terminal, the personal data including at least one of physical state information of the user, private information of the user, health care history information of the user and audio/video content preference information of the user;

a sensor unit which monitors a sleeping state of the user based on the personal data downloaded from the portable user terminal; and a control unit which controls one or more functions of the personally customized bed based on a result of the monitoring, and connects the personally customized electronic furniture to a health care system through a network when the connection to the health care system is selected through user interface, wherein the personal data is not directly measured from the user but downloaded from the portable user terminal, and includes non-sleep related private personal information.

\* \* \* \* \*